(12) United States Patent
Tranchina et al.

(10) Patent No.: US 8,179,190 B2
(45) Date of Patent: *May 15, 2012

(54) PULSE GENERATOR HAVING AN EFFICIENT FRACTIONAL VOLTAGE CONVERTER AND METHOD OF USE

(75) Inventors: Benjamin A Tranchina, Allen, TX (US); John H Erickson, Plano, TX (US); Anthony J Varrichio, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/185,114

(22) Filed: Jul. 18, 2011

(65) Prior Publication Data

US 2011/0273225 A1   Nov. 10, 2011

Related U.S. Application Data

(63) Continuation of application No. 12/426,053, filed on Apr. 17, 2009, now Pat. No. 7,982,529, which is a continuation of application No. 11/345,584, filed on Jan. 31, 2006, now abandoned.

(60) Provisional application No. 60/648,556, filed on Jan. 31, 2005.

(51) Int. Cl.
*G05F 1/10* (2006.01)
*G05F 3/02* (2006.01)

(52) U.S. Cl. ............................. 327/536; 607/2

(58) Field of Classification Search .................. 327/536; 363/59–60

See application file for complete search history.

(56) References Cited

U.S. PATENT DOCUMENTS

| | | | |
|---|---|---|---|
| 5,948,004 A | 9/1999 | Weijand et al. | |
| 5,964,787 A | 10/1999 | Kerver et al. | |
| 5,999,040 A | 12/1999 | Do et al. | |
| 6,198,645 B1 | 3/2001 | Kotowski et al. | |
| 7,805,189 B2 | 9/2010 | Stein et al. | |
| 7,949,393 B2 * | 5/2011 | Varrichio et al. | 607/2 |
| 2002/0068957 A1 * | 6/2002 | Wolfe et al. | 607/2 |
| 2003/0058666 A1 | 3/2003 | Myono | |
| 2004/0167407 A1 | 8/2004 | Roberts | |

FOREIGN PATENT DOCUMENTS

WO    9962594    12/1999

OTHER PUBLICATIONS

European Patent Office, Search Report for EP06250376 dated Jun. 29, 2006.

* cited by examiner

*Primary Examiner* — Quan Tra
(74) *Attorney, Agent, or Firm* — Christopher S. L. Crawford; Craig Hoersten; Peter R. Lando

(57) ABSTRACT

Disclosed are systems and methods which provide voltage conversion in increments less than integer multiples of a power supply (e.g., battery) voltage. A representative embodiment provides power supply voltage multipliers in a binary ladder distribution to provide a desired number of output voltage steps using a relatively uncomplicated circuit design. By using different sources in various combinations and/or by "stacking" different sources in various ways, the voltage multiplier circuit may be used to provide desired voltages. In order to minimize the number of components used in a voltage converter of an embodiment, a capacitive voltage converter circuit uses one or more storage capacitors in place of pump capacitors in a voltage generation cycle. Also, certain embodiments do not operate to generate an output voltage until the time that voltage is needed.

6 Claims, 2 Drawing Sheets

PULSE GENERATOR HAVING AN EFFICIENT FRACTIONAL VOLTAGE CONVERTER AND METHOD OF USE

CROSS-REFERENCE TO RELATED APPLICATIONS

This application is a continuation of U.S. application Ser. No. 12/426,053, filed Apr. 17, 2009, now U.S. Pat. No. 7,982,529, which is a continuation of U.S. application Ser. No. 11/345,584, filed Jan. 31, 2006, abandoned, which claims the benefit of U.S. Provisional Application No. 60/648,556, filed Jan. 31, 2005, the disclosure of which is incorporated herein by reference. The present application is related to and commonly assigned U.S. application Ser. No. 11/105,191, filed Apr. 12, 2005, now U.S. Pat. No. 7,450,987, U.S. application Ser. No. 11/122,540, filed May 5, 2005, abandoned, and U.S. application Ser. No. 11/105,332, filed Apr. 12, 2005, now U.S. Pat. No. 7,180,760, the disclosures of which are hereby incorporated herein by reference.

TECHNICAL FIELD

This application relates generally to power supply circuitry and, more particularly, to an efficient voltage multiplier.

BACKGROUND OF THE INVENTION

A variety of devices employ power supply circuitry in order to provide voltages and/or currents used in operating the device itself or used in the operation of the device. Such power supply circuitry is often utilized to alter power supplied from a power source, such as line power or a battery, to meet the demands or requirements of the device. For example, power supply circuitry may be utilized to step-up/step-down current, step-up/step-down voltage, provide a direct current (DC) output from an alternating current (AC) input, and/or provide an AC output from a DC input. Circuitry providing the foregoing may be relatively complex, perhaps including a number of active components, and often suffers from inefficiencies, e.g., an appreciable amount of the power supply energy is consumed in altering the power supplied from the power source. However, complex and inefficient power supply circuits are undesirable in a number of situations, such as in certain portable devices using a battery as a power supply.

An implantable neurostimulator, such as the GENESIS™ Neurostimulation System available from Advanced Neuromodulation Systems, Plano Tex., is one example of a portable device which may implement power supply circuitry as described above in altering one or more aspects of a battery power supply output for use in operating the device or in the operation of the device. Because implanting and explanting such a neurostimulator causes appreciable trauma to the patient, it is typically desired that the neurostimulator power supply be small and relatively long lived and that the circuitry (including power supply circuitry) of the neurostimulator be small and reliable. Even where a rechargeable battery is used as a power supply, it is typically desired to provide operation of the neurostimulator in such a way as to result in a relatively long battery life between recharge cycles so as to minimize restrictions on the patient's mobility. Battery voltage associated with a battery such as may be implemented in a neurostimulator can be 2.5 volts, for example, or on the order of 4.2 volts, for lithium ion, but in any case is typically relatively low due to the size constraints of the device.

In providing neurostimulation, it may be desirable to provide up to 30 milliamp pulses, for example, to an area of the patient's anatomy, such as near the spinal cord. The patient equivalent resistance in the area of the delivery of the therapeutic current can often range from 200 ohms to 2 kilohms. Knowing the current and load, the voltage needed to effect the desired therapy can be calculated in the above example as being on the order of 15 volts to provide the desired current to the patient. However, as described above, the battery voltage may be much less than 15 volts.

Accordingly, the above mentioned neurostimulator may implement power supply circuitry which provides voltage up-conversion to facilitate delivery of therapy to the patient using the available power supply. There are many ways to implement voltage up-conversion. However, in a battery powered device, in particular, it is generally desirable to provide the voltage up-conversion in the most efficient way possible.

In the past a number of power supply circuit configurations have been implemented to provide voltage up-conversion. In particular, inductive voltage up-converters (voltage up-converters also being referred to herein as voltage multipliers) and capacitive voltage up-converters.

Inductive voltage up-converters or voltage multipliers require the use of a coil for voltage conversion, which in turn necessitates the use of alternating current. However, batteries such as those used in the above mentioned neurostimulators provide direct current. Accordingly, the use of an inductive voltage multiplier with a battery power supply generally involves the use of complicated and inefficient switching regulator circuitry to convert the direct current from the battery to alternating current for voltage up-conversion. Moreover, additional rectifier circuitry is typically implemented to convert the up-converted alternating current back to direct current. Electromagnetic noise is often introduced by inductor-based switching regulator circuitry, such as may interfere with data communications, thereby requiring additional shielding and/or circuitry to prevent such electromagnetic noise from interfering with operation of the device. Accordingly, inductive voltage up-converters are generally undesirable for use in small battery powered devices, such as implantable neurostimulators.

Capacitive voltage up-converters or voltage multipliers have generally been used to provide output voltages in integer multiples of the battery voltage (e.g., 2 times the battery voltage, 3 times the battery voltage, etcetera). However, such integer multiples of the battery voltage often are not the most efficient voltages. For example, assuming a battery voltage of 4 volts and that a desired current for therapeutic stimulation requires 9 volts, a typical prior art capacitive voltage multiplier must provide 12 volts for the needed 9 volt pulse because its design provides selection between 4 volts (1 times the 4 volt battery voltage), 8 volts (2 times the 4 volt battery voltage), 12 volts (3 times the 4 volt battery voltage), etcetera.

The power consumed from the battery is based on the multiplicative factor created from the battery. In the foregoing example, if 10 milliamps was delivered to the patient, 30 milliamps was pulled from the battery because of the 3 times multiplicative factor used in the voltage up-conversion. Accordingly, if the voltage provided by the power supply circuitry could be controlled to more closely match that needed for the desired level of stimulation, the multiplicative factor, and thus the power pulled from the battery, could be reduced.

Further compounding the inefficiencies associated with capacitive voltage multipliers of the prior art is their operation in creating and storing a voltage multiple. In operation, a capacitive voltage multiplier will create a particular multiply voltage and store that voltage on a storage capacitor for output by the power supply circuit. When it is desired to change the output voltage of the power supply circuit, the previously stored multiply voltage stored by the storage capacitor must be discharged in order to change the voltage to a new value. The discharge of the previously stored multiply voltage is a waste of energy which, if done often, can amount to an appreciable drain on the power supply. For example, where two sequential stimulation pulses of a neurostimulator require different voltages, prior art capacitive voltage multipliers would require discharging of capacitors charged for providing the first voltage for recharging of the capacitors for providing the second voltage, thereby wasting energy.

Accordingly, a need exists in the art for an efficient voltage multiplier, such as may be used in relatively small, battery powered devices.

BRIEF SUMMARY OF THE INVENTION

The present application is directed to systems and methods which provide voltage conversion in increments less than integer multiples (i.e., fractions) of a power supply (e.g., battery) voltage. Some representative embodiments provide a plurality of different power supply voltage multipliers, including fractional multipliers. Additionally or alternatively, some representative embodiments provide a plurality of different power supply voltage dividers, including fractional dividers.

A representative embodiment provides power supply voltage multipliers and/or dividers in a binary ladder distribution to provide a desired number of output voltage steps using a circuit design which may readily be implemented in an integrated circuit or integrated circuits. For example, a capacitive voltage multiplier provided according to a representative embodiment may comprise a voltage doubler generating twice the battery voltage, the battery itself generating the battery voltage, a voltage halfer generating half of the battery voltage, and a voltage quarterer generating a quarter of the battery voltage. Circuitry of the foregoing voltage multiplier preferably operates to combine the different voltages to provide a range of output voltages in one-quarter battery voltage ($\frac{1}{4} V_B$), or other power source voltage steps. By using these different sources in various combinations and/or by "stacking" these different sources in various ways, the voltage multiplier circuit may be used to provide desired voltages. For example, the output voltage of such a voltage multiplier may range from $\frac{1}{4} V_B$ to $3\frac{3}{4} V_B$, in one-quarter battery voltage steps. Accordingly, representative embodiments may be controlled to provide an output voltage more near that desired than would otherwise be available using a conventional capacitive voltage conversion circuit configuration.

In order to minimize the number of components used in a voltage converter of a representative embodiment, a capacitive voltage converter circuit uses one or more storage capacitors in place of pump capacitors in a voltage generation cycle. In past capacitive voltage multiplier circuits, pump capacitors have been used to generate a voltage from the power supply and storage capacitors have been used in storing the generated voltage until output, and the use of these capacitors as pump or storage capacitors has been mutually exclusive. However, representative embodiments use some of the storage capacitors in place of pump capacitors in order to reduce the number of components used in providing a conversion circuit. Moreover, representative embodiments utilize pump and storage capacitors which are not matched (e.g., not of the same capacitance) when generating voltages. According to a representative embodiment, storage capacitors are relatively large whereas pump capacitors are relatively small, although a combination of storage and pump capacitors is used in generating a particular voltage multiple or fraction of a voltage.

Representative embodiments do not operate to generate an output voltage until the time that voltage that is needed. For example, by stacking the supply capacitors (e.g., pump capacitors and/or storage capacitors) to form the desired output voltage as that voltage is being requested, representative embodiments avoid a need to discharge a particular source capacitor in order to change the output voltage. Instead, representative embodiments operate to stack the supply capacitors as needed to provide a desired output voltage. Accordingly, there is no energy wasted in the formation of the desired voltage according to some embodiments.

As can be appreciated from the foregoing, some representative embodiments provide an efficient voltage multiplier, such as may be used in relatively small, battery powered devices.

The foregoing has outlined rather broadly the features and technical advantages of some embodiments in order that the detailed description that follows may be better understood. Additional features and advantages will be described hereinafter. It should be appreciated that the conception and specific embodiments disclosed may be readily utilized as a basis for modifying or designing other structures for carrying out the same purposes. It should also be realized that such equivalent constructions do not depart from the appended claims. The novel features with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWING

For a more complete understanding of the present application, reference is now made to the following descriptions taken in conjunction with the accompanying drawing, in which.

DETAILED DESCRIPTION OF THE INVENTION

In order to aid the reader in understanding the concepts of some embodiments, a representative embodiment is described herein with reference to a neurostimulation system. Such a system generally has several design constraints associated therewith, such as limited battery power, small size, high reliability, and efficient operation, particularly relevant to advantages available from voltage converters implementing concepts. However, it should be appreciated that voltage converters provided according to some embodiments may be used in any number host systems or situations. Exemplary embodiments are described herein with reference to providing voltage multiplication. However, one of ordinary skill in the art will readily appreciate that concepts disclosed in relation to voltage multipliers are applicable to voltage dividers as well.

Figure 1:
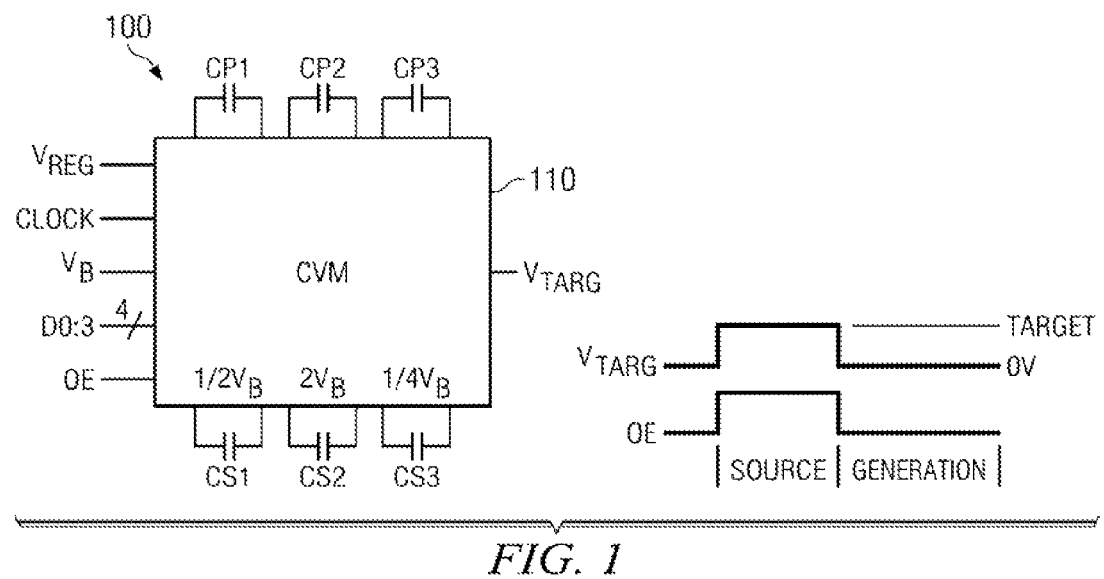
FIG. 1 shows a high level block diagram of a voltage multiplier configuration of a representative embodiment.

Directing attention to FIG. 1, a high level block diagram of a voltage multiplier configuration of a representative embodiment is shown as voltage multiplier 100. Voltage multiplier 100 of the illustrated embodiment includes capacitive voltage multiplier (CVM) integrated circuit 110, pump capacitors CP1, CP2, and CP3, and storage capacitors CS1, CS2, and CS3. CVM 110 includes signal inputs $V_{REG}$, CLOCK, $V_B$, D0:3 and OE, and output $V_{TARG}$.

$V_{REG}$ of the illustrated embodiment provides a regulated voltage input for use by circuits (e.g., digital control circuits) of CVM 110 in providing voltage multiplication. $V_{REG}$ is typically at a logic level (e.g., 2.2 volts) which is lower than the power supply voltage (e.g., $V_B$). CLOCK is a system clock signal used for synchronizing operation of aspects of CVM 110 with operation of aspects of a host system, such as for digital communication, voltage output timing, etcetera. $V_B$ provides a power supply voltage level input for use in voltage multiplication by CVM 110. For example, $V_B$ may provide unregulated battery voltage input, such as 4.1 volts where a lithium-ion battery is used. D0:3 provides a digital input signal. In the illustrated embodiment, D0:3 provides a 4 bit digital signal which is used in selecting a desired output voltage level. OE provides an output enable signal to selectively enable the output voltage $V_{TARG}$. Accordingly, a signal provided at OE may comprise a binary logic level signal. $V_{TARG}$ provides a target output voltage level as selected under control of D0:3 and as enabled under control of OE. Further detail with respect to the circuitry of CVM 110 according to one representative embodiment is provided below with reference to FIG. 5.

Pump capacitors CP1, CP2, and CP3 of the illustrated embodiment are utilized in a voltage generation cycle. Because of the use of a partitioned circuit configuration of CVM 100 of a representative embodiment, as will be better understood from the discussion which follows, and the relatively low voltages experienced by capacitors CP1, CP2, and CP3, these pump capacitors may be relatively small, such as on the order of 0.5 μFarads. One or more of storage capacitors CS1, CS2, and CS3 may be stacked in providing a desired output voltage ($V_{TARG}$) such that a relatively high voltage is experienced thereby. Moreover, in order to sustain a relatively constant (i.e., flat) output voltage level during a voltage output cycle, storage capacitors CS1, CS2, and CS3 may be larger than the pump capacitors, such as on the order of 100 μFarads. Accordingly, various capacitors utilized in generating a particular voltage multiple or voltage fraction need not be matched. For example, according to a representative embodiment where pump capacitors are used in combination with storage capacitors to generate a voltage multiple or voltage fraction, are not matched.

It should be appreciated that through controlled stacking of the various capacitors in providing a desired output voltage, the maximum voltage levels experienced by particular capacitors (and other components) may be minimized. Therefore, one or more of the capacitors or other circuitry may be sized differently with respect to one another according to some embodiments. Accordingly, various ones of the pump capacitors may be sized differently with respect to other pump capacitors and/or various ones of the storage capacitors may be sized differently with respect to other storage capacitors.

In operation according to a representative embodiment, CVM 110 provides selectable voltage output at $V_{TARG}$ from 0 $V_B$ through 3¾ $V_B$ in ¼ $V_B$ steps. For example, a logic low input at OE may be used to turn the voltage output at $V_{TARG}$ off (0 $V_B$), such as during a voltage generation cycle. A logic high input at OE in combination with a particular bit combination logic input at D0:3 may be used to turn the voltage output at $V_{TARG}$ on and select a particular voltage level from ¼ $V_B$ through 3¾ $V_B$. Other fractional voltages may be provided through the use of combinations of capacitors different than those of the exemplary embodiment.

Generation of voltages using a voltage conversion circuit may include a plurality of phases, wherein during one or more such phases an output of the voltage conversion circuit may be disabled. For example, a charge phase may be used to charge the pump capacitors with current from the power supply and a pump phase may be used to pump the current into storage capacitors (the combination of these phases being referred to as a generation phase). A source phase may be used to output a desired voltage using an appropriate configuration of pump capacitors and/or storage capacitors. FIGS. 2A-4B illustrate interconnection of pump and storage capacitors in a charge phase (FIGS. 2A, 3A, and 4A) and a pump phase (FIGS. 2B, 3B, and 4B) according to a representative embodiment.

Figure 2A:
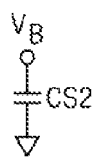
FIGS. 2A, 3A, and 4A show interconnection of pump and storage capacitors in a charge phase according to a representative embodiment.
Figure 2B:
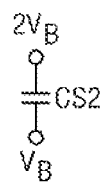
FIGS. 2B, 3B, and 4B show interconnection of pump and storage capacitors in a pump phase according to a representative embodiment.

FIGS. 2A and 2B illustrate a charge phase and pump phase, respectively, of a 2 $V_B$ source according to a representative embodiment. In the charge phase of FIG. 2A, capacitor CS2 is coupled between the power supply voltage ($V_B$) and ground in order to be charged to $V_B$. Thereafter, during the pump phase of FIG. 2B, the lead of capacitor CS2 formerly coupled to ground is coupled to $V_B$ to be pumped to twice the power supply voltage (2 $V_B$). This provides the 2 $V_B$ source of a voltage binary ladder of a representative embodiment. It should be appreciated that the above described charge and pump phases utilize a same capacitor, here CS2, thereby avoiding the use of separate pump and storage capacitors in providing a 2 $V_B$ source. Capacitor CS2 may be coupled to output $V_{TARG}$ of CVM integrated circuit 110, perhaps in a "stack" including other capacitors, to provide a desired voltage level output during a source phase.

Figure 3A:
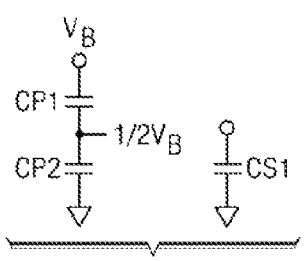
Figure 3B:
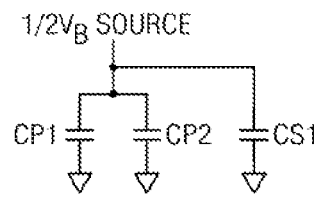

FIGS. 3A and 3B illustrate a charge phase and pump phase, respectively, of a ½ $V_B$ source according to a representative embodiment. In the charge phase of FIG. 3A, capacitors CP1 and CP2 are coupled in series between the power supply voltage ($V_B$) and ground in order to charge each capacitor to ½ $V_B$. In the illustration of FIG. 3A, capacitor CS1 is not utilized in charging the capacitors CP1 and CP2 and, therefore, is illustrated as disconnected therefrom. During the pump phase of FIG. 3B, the lead of capacitor CP1 formerly coupled to a lead of capacitor CP2 is coupled to ground and the capacitors are coupled in parallel with capacitor CS1 to pump capacitor CS1 to ½ the power supply voltage (½ $V_B$). Capacitor CS1 provides the ½ $V_B$ source of a voltage binary ladder of a representative embodiment. Capacitor CS2 may be decoupled from capacitors CP1 and CP2 and coupled to output $V_{TARG}$ of CVM integrated circuit 110, perhaps in a "stack" including other capacitors, to provide a desired voltage level output during a source phase.

Figure 4A:
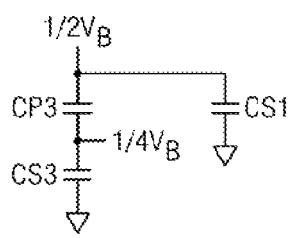
Figure 4B:
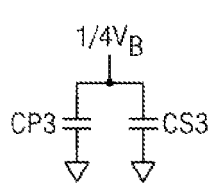
Figure 4C:
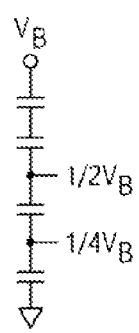
FIG. 4C shows one possible configuration of capacitors coupled in series to a power supply voltage ($V_B$) to provide $\frac{1}{4} V_B$.

FIGS. 4A and 4B illustrate a charge phase and pump phase, respectively, of a ¼ $V_B$ source according to a representative embodiment. It should be appreciated that 4 capacitors coupled in series to the power supply voltage ($V_B$) may be utilized in providing ¼ $V_B$, as shown in FIG. 4C. However, it was realized in the development of some embodiments that a ½ $V_B$ charge circuit (the lower half of the circuit shown in FIG. 4C) is provided in the circuitry of FIGS. 3A and 3B. Moreover, experimentation has revealed that, when capacitor CS1 is coupled to the ½$V_B$ point in the charge circuit of FIG. 3A, an equilibrium is reached, such that this capacitor may be relied upon to provide current in both the charge and pump phases. As such, in the charge phase of FIG. 4A, capacitors CP3 and CS3 are coupled in series between ½ the power supply voltage (½ $V_B$), as provided by capacitor CS1, and ground in order to charge each capacitor to ¼ $V_B$. Thereafter, during the pump phase of FIG. 4B, the lead of capacitor CP3 formerly coupled to a lead of capacitor CS3 is coupled to ground and the capacitors are coupled in parallel to pump capacitor CS3 to ¼ the power supply voltage (¼ $V_B$). This provides the ¼ $V_B$ source of a voltage binary ladder of a representative embodiment. It should be appreciated that the above described charge and pump phases reduce the number of capacitors utilized in providing a ¼ $V_B$ source, as compared to the circuit configuration of FIG. 4C. Capacitor CS3 may be decoupled from capacitor CP3 and coupled to output $V_{TARG}$ of CVM integrated circuit 110, perhaps in a "stack" including other capacitors, to provide a desired voltage level output during a source phase.

The forgoing charge and pump phases provide a ¼$V_B$, a ½ $V_B$, and a 2 $V_B$ source of a voltage binary ladder. The power supply voltage itself may be utilized in providing a $V_B$ source. These 4 sources may be used in various combinations and/or stacked in various ways for a source phase to provide a desired output voltage ($V_{TARG}$) in the range from ¼ $V_B$ to 3¾ $V_B$, in one-quarter $V_B$ steps. Stacking of the sources to provide an output voltage may be provided upon demand, such that the output voltage is generated at the time that voltage is needed. Such an on-demand output voltage generation technique avoids the situation in which a previously charged storage capacitor must be discharged in order to accommodate a change in desired output voltage. On-demand output voltage generation techniques of some embodiments are particularly efficient in delivery of pulses of asymmetric shapes and/or having different amplitudes. For example, where CVM integrated circuit 110 is utilized for voltage output in a neurostimulation device implementing a multi-stimulation set program (e.g., interleaving various stimulation voltages or amplitudes in successive stimulation pulses), the on-demand output voltage generation technique of come embodiments will provide efficient operation (e.g., extending battery life). The above reference patent application entitled "Multi-Programmable Trial Stimulator" provides detail with respect to a neurostimulation device implementing a multiple stimulation set as may benefit from implementation of one of the representative embodiments.

Controllable switching circuitry is preferably utilized in coupling capacitors in the various circuit configurations of FIGS. 2A-4B as well as to select sources and provide stacking for output of a desired voltage level. Such switching circuitry preferably provides a "break-before-make" connection so as to avoid overlapping connection of components between various circuit configurations (e.g., between a charge phase circuit configuration and a pump phase circuit configuration). The foregoing switching circuitry may be comprised of solid state circuitry such as bipolar devices, metal-oxide-silicon field effect transistors (MOSFETs), micro electromechanical systems (MEMS) devices (e.g., thermally actuated MEMS, electrostatically actuated MEMS, electromagnetically actuated MEMS), etcetera.

Figure 5:
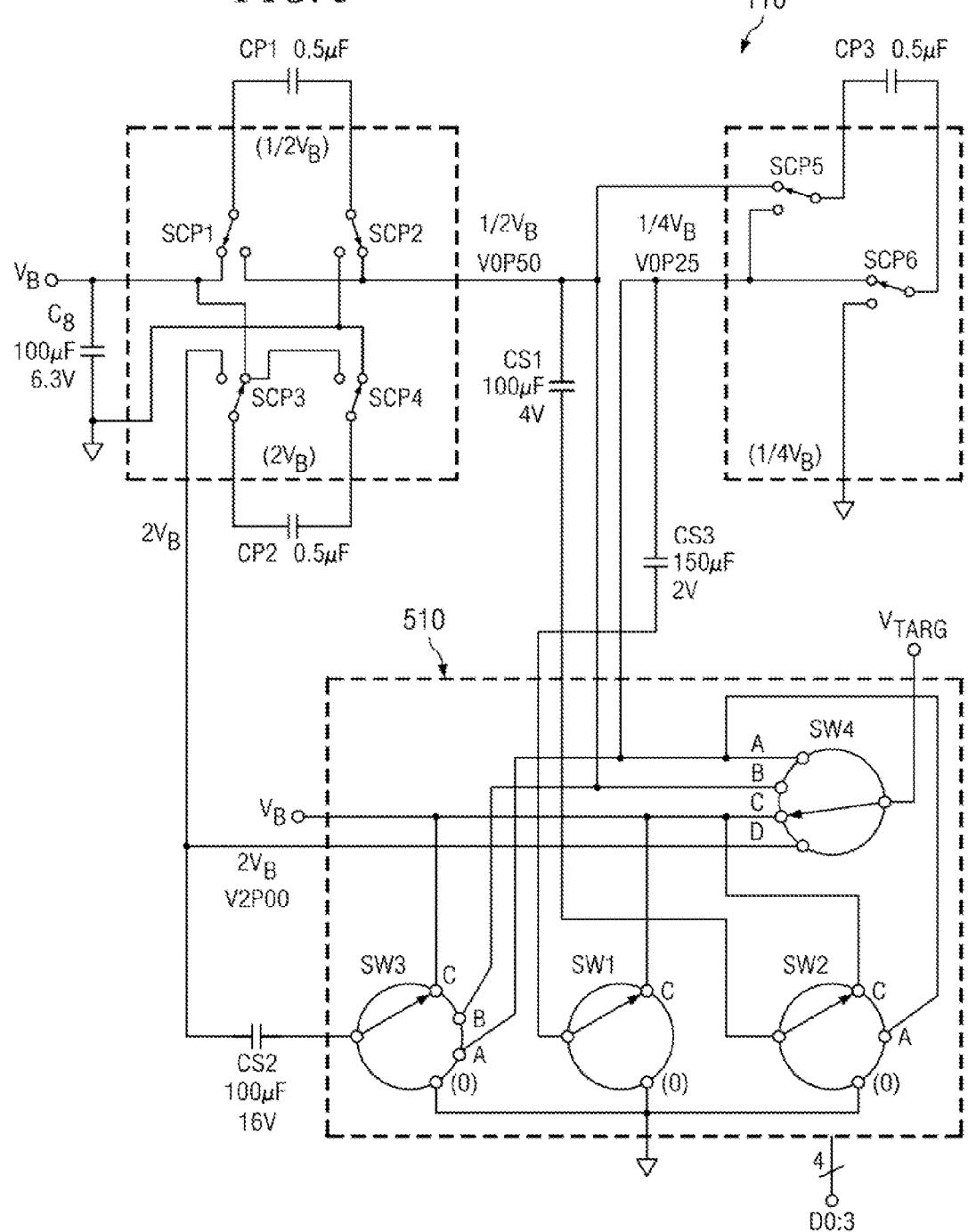
FIG. 5 shows detail with respect to the voltage multiplier circuitry of FIG. 1 according to a representative embodiment.

Directing attention to FIG. 5, detail with respect to controllable switching circuitry as may be provided in an integrated circuit of CVM 110 according to a representative embodiment is shown. It should be appreciated that the circuitry of FIG. 5 may be provided in one or more integrated circuits, according to some embodiments. In the embodiment of FIG. 5, switches SCP1-SCP6 provide switching between charge and pump circuit configurations to provide connection of the capacitors as shown in FIGS. 2A-4B. Control of switches SCP1-SCP6 is provided such that the charge phase is of sufficient duration to charge the capacitors used as pump capacitors and the pump phase is of sufficient duration for the capacitors used as pump capacitors to pump the capacitors used as source capacitors. According to some embodiments, the charge and pump phases are completed within a voltage generation cycle of the voltage multiplier. Thereafter, a source cycle of the voltage multiplier is invoked to provide output of a desired voltage. The source cycle is preferably of sufficiently long duration to provide desired energy output (e.g., provide a neurostimulator stimulation pulse of a desired length) and of sufficiently short duration to avoid draining the source capacitors (e.g., resulting in an unacceptable voltage droop). The foregoing timing may be established using a system clock signal, such as that provided at the CLOCK input of CVM 110 shown in FIG. 1.

In the representative embodiment illustrated in FIG. 5, control signals are provided to voltage selection circuitry 510, such as may be provided at the D0:3 input of CVM 110, in order to select a desired output voltage ($V_{TARG}$). Specifically, voltage selection circuitry 510 includes switches SW1-SW4 which may be controlled to provide selection of $V_{TARG}$ in a range from ¼ $V_B$ to 3¾ $V_B$. Representative information of control of switches SW1-SW4 in providing selection of output voltage levels according to a representative embodiment is provided in the following table.

| Control Signal D0:3 (D, C, B, A) | Output Voltage $V_{TARG}$ | Switch On |
|---|---|---|
| 0000 | Off | None |
| 0001 | ¼ $V_B$ | 4-A, 1-0 |
| 0010 | ½ $V_B$ | 4-B, 2-0 |
| 0011 | ¾ $V_B$ | 4-B, 1-0, 2-A |
| 0100 | $V_B$ | 4-C |
| 0101 | 1¼ $V_B$ | 4-A, 1-C |
| 0110 | 1½ $V_B$ | 4-B, 2-C |
| 0111 | 1¾ $V_B$ | 4-B, 1-C, 2-A |
| 1000 | 2 $V_B$ | 4-D |
| 1001 | 2¼ $V_B$ | 4-D, 3-A |
| 1010 | 2½ $V_B$ | 4-D, 3-B |
| 1011 | 2¾ $V_B$ | 4-D, 2-A, 3-B |
| 1100 | 3 $V_B$ | 4-D, 3-C |
| 1101 | 3¼ $V_B$ | 4-D, 1-C, 3-A |
| 1110 | 3½ $V_B$ | 4-D, 2-C, 3-B |
| 1111 | 3¾ $V_B$ | 4-D, 1-C, 2-A, 3-B |

It should be appreciated that the foregoing circuitry facilitates selection of output voltage levels with a resolution heretofore unavailable in a capacitive voltage multiplier design well suited for use in applications such as implantable neurostimulator devices. For example, in operation of the foregoing, the output voltage level may be chosen as 1¼ $V_B$, 1½ $V_B$, or 1¾ $V_B$, which ever more closely matches a desired output voltage level. Where the power supply comprises a lithium-ion battery providing 4.1 volts ($V_B$), approximately 1 volt increments are provided between each of the above selections. The difference in power consumption associated with a voltage multiplier able to more closely match the desired output voltage level can be quite significant. For example, the power savings associated with selection of 1¼ $V_B$ by operation of a voltage multiplier (where $1\frac{1}{4} V_B$ provides an output voltage level at least as high as that desired) over selection of $2 V_B$ of a typical prior art is on the order of 37½% power savings. Accordingly, a battery may last as much as 37½% longer in an implantable neurostimulator implementing a voltage multiplier. Likewise, recharge cycle time associated with a rechargeable battery device may be increased as much as 37½%, by implementing a voltage multiplier. Accordingly, if such a device required recharging every 18 hours using a typical voltage multiplier, the device might be operated with a recharge every 24 hours by using a voltage multiplier.

Moreover, circuit configurations used according to some embodiments provide efficiencies with respect to power consumed by the voltage multiplier circuitry itself. For example, circuitry used in providing various levels of voltage multiplication are partitioned in the representative embodiment illustrated in FIG. 5 so as to reduce the maximum voltage levels experienced by particular components. In particular, the partitioning of some embodiments provides stacking of components in providing a desired output voltage level such that the majority of devices (e.g., switches and capacitors) do not experience high voltages (e.g., $3 V_B$), although these devices are used in generating the highest voltages available from the voltage multiplier. Accordingly, many of the devices used in a voltage multiplier may be designed to handle lower voltages, and thus perhaps be smaller, introduce less resistance, etcetera, whereas only a few of the devices may be designed to handle the maximum voltage levels provided by the voltage multiplier. Such a configuration may be particularly useful in an integrated circuit configuration, such as that of CVM 110 shown in FIG. 1, wherein MOSFET switches may be implemented. For example, the smaller a MOSFET switching device may be made, the less capacitance associated therewith, and the less power consumption associated with its operation.

Providing the foregoing switches as MOSFET switches or other transmission gates, and making gates as low voltage as possible, as discussed above, allows lower voltage control signals to operate these switches. Accordingly, the digital control signals provided at input D0:3 of CVM 110 of FIG. 1 may be utilized to drive a number of these switches directly. Level shifters may be implemented to drive switches associated with the higher voltage partitions of the voltage multiplier circuit according to some embodiments. However, it should be appreciated that the above described technique of partitioning the circuitry of the voltage multiplier minimizes the number of level shifters used in providing the optimum level control signals to the switches.

The foregoing voltage multiplier configuration provides a representative embodiment providing relatively fine output voltage level increments with a relatively small number of components. In particular, the switching circuitry may readily be implemented in an integrated circuit with a small number of external components (e.g., a minimum number of external capacitors). Moreover, the illustrated embodiment has provided a balance between providing fine enough control of output voltage level selection to maximize power efficiency while minimizing the area and external components, and thus balances between the size and power consumption of the circuitry and the resulting power efficiency.

Although the representative embodiments above have been described with reference to providing output voltage level selection in ¼ power supply voltage increments, the concepts of some embodiments are scalable and may be used in providing voltage multipliers providing different increments (e.g., ¹⁄₁₆, ⅛, ⅕, ⅓, etcetera) of a power supply voltage.

Moreover, although the discussion above has made reference to a power supply voltage, some embodiments may be utilized with respect to any voltage available as an input to the voltage conversion circuit, including regulated, filtered, and level shifted voltages from any of a number of sources. Likewise, embodiments are not limited in application to battery power supplies, and may be used with respect to any number of sources, including line sources.

Some embodiments of fractional voltage conversion circuits have been described herein with respect to providing desired power supply voltage level output. However, the present concepts of voltage multiplication are not limited to use with respect to providing a power supply. For example, embodiments may be utilized to provide a high power digital to analog converter that provides voltage level output above a power supply voltage level.

Although some embodiments and advantages have been described in detail, it should be understood that various changes, substitutions and alterations can be made herein without departing from the appended claims. Moreover, the scope of the appended claims is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of operating an implantable pulse generator (IPG) for generating electrical pulses for application to tissue of a patient, the method comprising:
   operating a battery for powering the IPG;
   operating a voltage conversion module coupled to the battery for generating an output voltage that is selected from a range of voltage levels including non-integer multiples of a battery voltage according to a control signal, wherein during pump phase operation, (i) the voltage conversion module charges a first storage capacitor to a first voltage level that is less than the battery voltage, and (ii) the voltage conversion modules charges a second storage capacitor to a second voltage level that is greater that the battery voltage;
   operating pulse generating circuitry for generating electrical pulses, wherein the pulse generating circuitry receives the output voltage from the voltage conversion module for pulse generation operations; and
   operating a controller for controlling the pulse generating circuitry to generate electrical pulses according to a stimulation program, the stimulation program including a first set of parameters including a first amplitude value and a second set of parameters including a second amplitude value, wherein during operation according to the stimulation program, the controller causes the pulse generating circuitry to repeatedly alternate between generating one or more pulses at the first amplitude value and generating one or more pulses at the second amplitude value;
   wherein, during operation according to the stimulation program, the controller sends a control signal to the voltage conversion module to select different voltage levels for the second voltage according to the first and second amplitude values;

wherein during operation according to the stimulation program, the voltage conversion module controls one or more switches to connect multiple storage capacitors to directly provide the output voltage according to the control signal from the controller without discharging the first and second capacitors.

2. The implantable pulse generator of claim 1 wherein the voltage conversion module further connects storage capacitors in series with the battery to directly provide the output voltage.

3. The implantable pulse generator of claim 1 wherein the voltage conversion module charges a third storage capacitor to a third voltage level that is less than the battery voltage.

4. The implantable pulse generator of claim 3 wherein the first voltage level is ½ of the battery voltage and the third voltage level is ¼ of the battery voltage level.

5. The implantable pulse generator of claim 1 wherein the second voltage level is 2 times the battery voltage.

6. The implantable pulse generator of claim 1 wherein the controller selects a lowest voltage level from the range of voltage levels sufficient for an amplitude value of a given pulse.

* * * * *